United States Patent
Shimane et al.

(10) Patent No.: US 10,308,642 B2
(45) Date of Patent: Jun. 4, 2019

(54) ANTI-HEPATITIS B VIRUS AGENT

(71) Applicants: FUJIFILM Toyama Chemical Co., Ltd., Tokyo (JP); PUBLIC UNIVERSITY CORPORATION NAGOYA CITY UNIVERSITY, Nagoya-shi, Aichi (JP)

(72) Inventors: Kazuki Shimane, Toyama (JP); Yasuhito Tanaka, Nagoya (JP)

(73) Assignees: FUJIFILM Toyama Chemical Co., Ltd., Tokyo (JP); PUBLIC UNIVERSITY CORPORATION NAGOYA CITY UNIVERSITY, Nagoya (JP)

( * ) Notice: Subject to any disclaimer, the term of this patent is extended or adjusted under 35 U.S.C. 154(b) by 0 days.

(21) Appl. No.: 15/765,011

(22) PCT Filed: Oct. 5, 2016

(86) PCT No.: PCT/JP2016/079614
§ 371 (c)(1),
(2) Date: Mar. 30, 2018

(87) PCT Pub. No.: WO2017/061466
PCT Pub. Date: Apr. 13, 2017

(65) Prior Publication Data
US 2018/0291011 A1    Oct. 11, 2018

(30) Foreign Application Priority Data
Oct. 5, 2015 (JP) ................. 2015-197725

(51) Int. Cl.
A61K 31/4422 (2006.01)
A61P 31/20 (2006.01)
C07D 409/04 (2006.01)
C07D 213/80 (2006.01)
A61K 31/443 (2006.01)
A61K 31/4436 (2006.01)
A61K 31/4439 (2006.01)
C07D 405/10 (2006.01)
C07D 409/10 (2006.01)

(52) U.S. Cl.
CPC ......... *C07D 409/04* (2013.01); *A61K 31/443* (2013.01); *A61K 31/4422* (2013.01); *A61K 31/4436* (2013.01); *A61K 31/4439* (2013.01); *A61P 31/20* (2018.01); *C07D 213/80* (2013.01); *C07D 405/10* (2013.01); *C07D 409/10* (2013.01)

(58) Field of Classification Search
CPC .. C07D 409/04; C07D 213/80; C07D 405/10; A61P 31/20

USPC ........................................ 546/276
See application file for complete search history.

(56) References Cited

U.S. PATENT DOCUMENTS 4,698,352 A * 10/1987 Narita ................. C07D 209/20
514/339
2012/0022255 A1    1/2012 Fujishita et al.

FOREIGN PATENT DOCUMENTS

| CN | 1465567 A | 1/2004 |
|---|---|---|
| CN | 103992290 A | 8/2014 |
| JP | 59-080665 A | 5/1984 |
| JP | 61-246163 A | 11/1986 |
| JP | 02-061947 B2 | 12/1990 |
| WO | 2010/110231 A1 | 9/2010 |

OTHER PUBLICATIONS

Pyridonecarboxylic acids as anti microbials, Hirokazi Narita et al (Year: 1986).*
Jane Laursen et al , Further Exploration of Antimicrobial Ketodihydronicotine Acid Derivatives by multiple parallel Syntheses (Year: 2006).*
Zhiliang LV et al., "Design, Synthesis, and Antihepatitis B Virus Activities of Novel 2-Pyridone Derivatives", Journal of Medicinal Chemistry, 2010, pp. 660-668, vol. 53, No. 2.
Internal Search Report for PCT/JP2016/079614, dated Nov. 1, 2016.
Ruma Rajbhandari et al, Treatment of Hepatitis B: A Concise Review, Clinical and Translational Gastroenterology, vol. 7, No. 9, Sep. 1, 2016, pp. e190 (10 pages total).
Debika Bhattacharya et al, Review of Hepatitis B Therapeutics, Clinical Infectious Diseases, vol. 51, No. 10, Nov. 15, 2010, pp. 1201-1208.
Extended European Search Report (EESR) in European Application No. 16853620.9 dated Apr. 23, 2019.

* cited by examiner

Primary Examiner — Rita J Desai
(74) Attorney, Agent, or Firm — Sughrue Mion, PLLC

(57) ABSTRACT

An anti-hepatitis B virus agent comprising a compound represented by general formula [1],

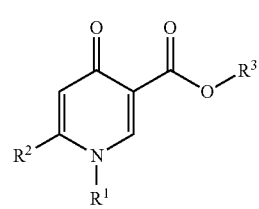

[1]

wherein $R^1$ represents an aryl group, which may be substituted, or the like; $R^2$ represents an aryl group, which may be substituted, or the like; and $R^3$ represents a hydrogen atom or the like; or a salt thereof.

9 Claims, No Drawings

ANTI-HEPATITIS B VIRUS AGENT

CROSS REFERENCE TO RELATED APPLICATIONS

This application is a National Stage of International Application No. PCT/JP2016/079614 filed Oct. 5, 2016, claiming priority based on Japanese Patent Application No. 2015-197725 filed Oct. 5, 2015.

TECHNICAL FIELD

The present invention relates to an anti-hepatitis B virus agent.

BACKGROUND ART

Hepatitis B, which is one of the viral hepatitides resulting from infection by the hepatitis B virus (HBV). It has been estimated that there are 350 million HBV infected people worldwide.

For the treatment of hepatitis B, an agent such as interferon or a nucleic acid analogue is used, but these treatments are not sufficiently effective.

Pyridone carboxylic acid derivatives having antibacterial activity are known (Patent Document 1). It is, however, not known that the pyridone carboxylic acid derivatives described in Patent Document 1 have antiviral activity.

PRIOR-ART DOCUMENTS

Patent Document

Patent Document 1: JP H2-61947 B

SUMMARY OF INVENTION

Technical Problem

An object of the present invention is to provide a novel anti-HBV agent.

Solution to Problem

Under these circumstances, the present inventors have found, through earnest studies, that a compound represented by general formula [1] or a salt thereof has excellent anti-HBV activity, thereby accomplishing the present invention.

Specifically, the present invention provides the following is defined as follows:

<1>
An anti-hepatitis B virus agent, comprising a compound represented by general formula [1]:

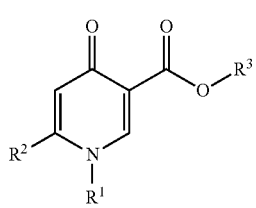

[1]

wherein $R^1$ represents an aryl group which may be substituted, or a heterocyclic group which may be substituted;
$R^2$ represents a $C_{3-8}$ cycloalkyl group which may be substituted, an aryl group which may be substituted, or a heterocyclic group which may be substituted; and
$R^3$ represents a hydrogen atom or a carboxyl protecting group, or a salt thereof.

<2>
The anti-hepatitis B virus agent according to <1>, wherein $R^1$ represents an aryl group which may be substituted.

<3>
The anti-hepatitis B virus agent according to <1>, wherein $R^1$ represents a phenyl group which may be substituted.

<4>
The anti-hepatitis B virus agent according to <1>, wherein $R^1$ represents a heterocyclic group which may be substituted.

<5>
The anti-hepatitis B virus agent according to <1>, wherein $R^1$ represents a bicyclic heterocyclic group which may be substituted.

<6>
The anti-hepatitis B virus agent according to any one of <1> to <5>, wherein $R^2$ represents an aryl group which may be substituted.

<7>
The anti-hepatitis B virus agent according to any one of <1> to <5>, wherein $R^2$ represents a phenyl group which may be substituted.

<8>
The anti-hepatitis B virus agent according to any one of <1> to <5>, wherein $R^2$ represents a heterocyclic group which may be substituted.

<9>
The anti-hepatitis B virus agent according to any one of <1> to <5>, wherein $R^2$ represents a monocyclic heterocyclic group which may be substituted.

Advantageous Effects of Invention

A compound represented by general formula [1] or a salt thereof according to the present invention has excellent anti-HBV activity, and hence is useful as an anti-hepatitis B virus agent.

DESCRIPTION OF EMBODIMENTS

The present invention will now be described in detail.

Herein, the symbol "%" means "% by mass" unless otherwise defined.

Herein, the following terms respectively have the following meanings unless otherwise defined.

A halogen atom means a fluorine atom, a chlorine atom, a bromine atom, or an iodine atom.

A $C_{1-3}$ alkyl group means a methyl group, an ethyl group, a propyl group, or an isopropyl group.

A $C_{1-6}$ alkyl group means a straight chain or branched chain $C_{1-6}$ alkyl group, such as a methyl group, an ethyl group, a propyl group, an isopropyl group, a butyl group, a sec-butyl group, an isobutyl group, a tert-butyl group, a pentyl group, an isopentyl group, and a hexyl group.

A $C_{3-8}$ cycloalkyl group means a $C_{3-8}$ cycloalkyl group such as a cyclopropyl group, a cyclobutyl group, a cyclopentyl group, and a cyclohexyl group.

An aryl group means a phenyl group or a naphthyl group.

An ar-$C_{1-6}$ alkyl group means an ar-$C_{1-6}$ alkyl group such as a benzyl group, a diphenylmethyl group, a trityl group, a phenethyl group, and a naphthylmethyl group.

A $C_{1-3}$ alkoxy group means a methoxy group, an ethoxy group, a propoxy group, or an isopropoxy group.

A $C_{1-6}$ alkoxy group means a straight chain or branched chain $C_{1-6}$ alkoxy group, such as a methoxy group, an ethoxy group, a propoxy group, an isopropoxy group, a butoxy group, an isobutoxy group, a sec-butoxy group, a tert-butoxy group, a pentyloxy group, and a hexyloxy group.

A $C_{1-6}$ alkoxy $C_{1-6}$ alkyl group means a $C_{1-6}$ alkoxy $C_{1-6}$ alkyl group such as a methoxymethyl group and a 1-ethoxyethyl group.

An ar-$C_{1-6}$ alkoxy $C_{1-6}$ alkyl group means an ar-$C_{1-6}$ alkoxy $C_{1-6}$ alkyl group such as a benzyloxymethyl group and a phenethyloxymethyl group.

A $C_{2-6}$ alkanoyl group means a straight chain or branched chain $C_{2-6}$ alkanoyl group, such as an acetyl group, a propionyl group, a valeryl group, an isovaleryl group, and a pivaloyl group.

An aroyl group means a benzoyl group or a naphthoyl group.

An acyl group means a formyl group, a $C_{2-6}$ alkanoyl group, or an aroyl group.

A $C_{1-6}$ alkoxycarbonyl group means a straight chain or branched chain $C_{1-6}$ alkoxycarbonyl group, such as a methoxycarbonyl group, an ethoxycarbonyl group, a propoxycarbonyl group, an isopropoxycarbonyl group, a tert-butoxycarbonyl group, and a 1,1-dimethylpropoxycarbonyl group.

An ar-$C_{1-6}$ alkoxycarbonyl group means an ar-$C_{1-6}$ alkoxycarbonyl group such as a benzyloxycarbonyl group and a phenethyloxycarbonyl group.

A $C_{1-6}$ alkylsulfonyl group means a $C_{1-6}$ alkylsulfonyl group such as a methylsulfonyl group, an ethylsulfonyl group, and a propylsulfonyl group.

An arylsulfonyl group means a benzenesulfonyl group, a p-toluenesulfonyl group, or a naphthalenesulfonyl group.

A $C_{1-6}$ alkylsulfonyloxy group means a $C_{1-6}$ alkylsulfonyloxy group such as a methylsulfonyloxy group, an ethylsulfonyloxy group, and a propylsulfonyloxy group.

An arylsulfonyloxy group means a benzenesulfonyloxy group, a p-toluenesulfonyloxy group, or a naphthalenesulfonyloxy group.

A $C_{1-3}$ alkylamino group means a methylamino group, an ethylamino group, a propylamino group, or an isopropylamino group.

A $C_{1-6}$ alkylamino group means a straight chain or branched chain $C_{1-6}$ alkylamino group, such as a methylamino group, an ethylamino group, a propylamino group, an isopropylamino group, a butylamino group, a sec-butylamino group, a tert-butylamino group, a pentylamino group, and a hexylamino group.

A di($C_{1-3}$ alkyl)amino group means a straight chain or branched chain di($C_{1-3}$ alkyl)amino group, such as a dimethylamino group, a diethylamino group, a dipropylamino group, a diisopropylamino group, an (ethyl)(methyl)amino group, and a (methyl)(propyl)amino group.

A di($C_{1-6}$ alkyl)amino group means a straight chain or branched chain di($C_{1-6}$ alkyl)amino group, such as a dimethylamino group, a diethylamino group, a dipropylamino group, a diisopropylamino group, a dibutylamino group, a di(tert-butyl)amino group, a dipentylamino group, a dihexylamino group, an (ethyl)(methyl)amino group, and a (methyl)(propyl)amino group.

A cyclic amino group means a cyclic amino group that contains one or more nitrogen atoms as a heteroatom forming the ring, and further may contain one or more oxygen atoms or sulfur atoms, such as azetidinyl, pyrrolidinyl, piperidinyl, homopiperidinyl, piperazinyl, homopiperazinyl, morpholinyl, homomorpholinyl, and thiomorpholinyl.

A monocyclic nitrogen-containing heterocyclic group means a monocyclic nitrogen-containing heterocyclic group containing a nitrogen atom alone as a heteroatom forming the ring, such as an azetidinyl group, a pyrrolidinyl group, a pyrrolinyl group, a pyrrolyl group, a piperidyl group, a tetrahydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a pyrazinyl group, a pyridazinyl group, a pyrimidinyl group, a homopiperazinyl group, a triazolyl group, and a tetrazolyl group.

A monocyclic oxygen-containing heterocyclic group means a tetrahydrofuranyl group, a furanyl group, a tetrahydropyranyl group, a dihydropyranyl group, or a pyranyl group.

A monocyclic sulfur-containing heterocyclic group means a thienyl group.

A monocyclic nitrogen- and oxygen-containing heterocyclic group means a monocyclic nitrogen- and oxygen-containing heterocyclic group containing a nitrogen atom and an oxygen atom alone as a heteroatom forming the ring, such as an oxazolyl group, an isooxazolyl group, an oxadiazolyl group, and a morpholinyl group.

A monocyclic nitrogen- and sulfur-containing heterocyclic group means a monocyclic nitrogen- and sulfur-containing heterocyclic group containing a nitrogen atom and a sulfur atom alone as a heteroatom forming the ring, such as a thiazolyl group, an isothiazolyl group, a thiadiazolyl group, a thiomorpholinyl group, a 1-oxidethiomorpholinyl group, and a 1,1-dioxidethiomorpholinyl group.

A monocyclic heterocyclic group means a monocyclic nitrogen-containing heterocyclic group, a monocyclic oxygen-containing heterocyclic group, a monocyclic sulfur-containing heterocyclic group, a monocyclic nitrogen- and oxygen-containing heterocyclic group, or a monocyclic nitrogen- and sulfur-containing heterocyclic group.

A bicyclic nitrogen-containing heterocyclic group means a bicyclic nitrogen-containing heterocyclic group containing a nitrogen atom alone as a heteroatom forming the ring, such as an indolinyl group, an indolyl group, an isoindolinyl group, an isoindolyl group, a pyrrolopyridinyl group, an indazolyl group, a benzimidazolyl group, a benzotriazolyl group, a tetrahydroquinolyl group, a dihydroquinolyl group, a quinolinyl group, a dihydroquinolinyl group, a tetrahydroisoquinolinyl group, a decahydroisoquinolinyl group, an isoquinolinyl group, a dihydroquinazolinyl group, a cinnolinyl group, a phthalazinyl group, a quinazolinyl group, a dihydroquinoxalinyl group, a quinoxalinyl group, a naphthylidinyl group, a purinyl group, a pteridinyl group, and a quinuclidinyl group.

A bicyclic oxygen-containing heterocyclic group means a bicyclic oxygen-containing heterocyclic group containing an oxygen atom alone as a heteroatom forming the ring, such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group, and a 1,4-benzodioxanyl group.

A bicyclic sulfur-containing heterocyclic group means a bicyclic sulfur-containing heterocyclic group containing a sulfur atom alone as a heteroatom forming the ring, such as a 2,3-dihydrobenzothienyl group and a benzothienyl group.

A bicyclic nitrogen- and oxygen-containing heterocyclic group means a bicyclic nitrogen- and oxygen-containing heterocyclic group containing a nitrogen atom and an oxygen atom alone as a heteroatom forming the ring, such as a dihydrobenzoxazolyl group, a benzoxazolyl group, a benzisooxazolyl group, a benzoxadiazolyl group, a benzomorpholinyl group, a dihydropyranopyridyl group, a dihydrodioxinopyridyl group, and a dihydropyridoxadinyl group.

A bicyclic nitrogen- and sulfur-containing heterocyclic group means a bicyclic nitrogen- and sulfur-containing heterocyclic group containing a nitrogen atom and a sulfur atom as a heterogroup forming the ring, such as a dihydrobenzothiazolyl group, a benzothiazolyl group, a benzoisothiazolyl group, and a benzothiadiazolyl group.

A bicyclic heterocyclic group means a bicyclic nitrogen-containing heterocyclic group, a bicyclic oxygen-containing heterocyclic group, a bicyclic sulfur-containing heterocyclic group, a bicyclic nitrogen- and oxygen-containing heterocyclic group, or a bicyclic nitrogen-sulfur-containing heterocyclic group.

A heterocyclic group means a monocyclic heterocyclic group or a bicyclic heterocyclic group.

Substituent group A: A halogen atom, a nitro group, a cyano group, a hydroxyl group which may be protected, a $C_{1-6}$ alkyl group which may be substituted with one or more groups selected from a substituent group B, an aryl group which may be substituted with one or more groups selected from substituent group B, a $C_{1-6}$ alkoxy group which may be substituted with one or more groups selected from substituent group B, a $C_{1-6}$ alkylamino group, a di($C_{1-6}$ alkylamino group, a heterocyclic group which may be substituted with one or more groups selected from substituent group B, and an oxo group.

Substituent group A1: A halogen atom, a hydroxyl group which may be protected, a $C_{1-3}$ alkyl group, and a $C_{1-3}$ alkoxy group.

Substituent group A2: A halogen atom, a phenyl group which may be substituted with one or more groups selected from a substituent group B1, a $C_{1-3}$ alkylamino group, a di($C_{1-3}$ alkyl)amino group, a cyclic amino group, and a monocyclic heterocyclic group.

Substituent group B: A halogen atom, a nitro group, a cyano group, a $C_{1-6}$ alkyl group, an aryl group, a $C_{1-6}$ alkoxy group, a $C_{1-6}$ alkylamino group, a di($C_{1-6}$ alkyl)amino group, a heterocyclic group, and an oxo group.

Substituent group B1: A halogen atom, a nitro group, and a cyano group.

A carboxyl protecting group includes all groups usable as a usual protecting group for a carboxyl group; examples include groups described in Greene's Protective Groups in Organic Synthesis, fifth edition, pp. 686-836, 2014, published by John Wiley & Sons, INC. Specific examples include a $C_{1-6}$ alkyl group, an ar-$C_{1-6}$ alkyl group, a $C_{1-6}$ alkoxy $C_{1-6}$ alkyl group, and an ar-$C_{1-6}$ alkoxy $C_{1-6}$ alkyl group. Such a group may be substituted with one or more groups selected from substituent group A.

A hydroxyl protecting group includes all groups usable as a usual protecting group for a hydroxyl group; examples include groups described in Greene's Protective Groups in Organic Synthesis, fifth edition, pp. 17-471, 2014, published by John Wiley & Sons, INC. Specific examples include a $C_{1-6}$ alkyl group, an ar-$C_{1-6}$ alkyl group, a $C_{1-6}$ alkoxy $C_{1-6}$ alkyl group, an acyl group, a $C_{1-6}$ alkoxycarbonyl group, an ar-$C_{1-6}$ alkoxycarbonyl group, a $C_{1-6}$ alkylsulfonyl group, an arylsulfonyl group, a tetrahydrofuranyl group, and a tetrahydropyranyl group. Such a group may be substituted with one or more groups selected from substituent group A.

Examples of a leaving group include a halogen atom, a $C_{1-6}$ alkyl sulfonyloxy group or an aryl sulfonyloxy group. Each of the $C_{1-6}$ alkyl sulfonyloxy group and the aryl sulfonyloxy group may be substituted with one or more groups selected from substituent group A.

A compound represented by general formula [1], as used in the present invention, is preferably a compound defined as follows:

$R^1$ represents an aryl group which may be substituted or a heterocyclic group which may be substituted.

The aryl group and the heterocyclic group of $R^1$ may be substituted with one or more groups selected from substituent group A.

A compound in which $R^1$ represents an aryl group which may be substituted is preferable; a compound in which $R^1$ represents a phenyl group which may be substituted, more preferable; and a compound in which $R^1$ represents a phenyl group which may be substituted with one or more groups selected from substituent group A1, further preferable.

In another aspect, a compound in which $R^1$ represents a heterocyclic group which may be substituted is preferable; a compound in which $R^1$ represents a bicyclic heterocyclic group which may be substituted, more preferable; and a compound in which $R^1$ represents a bicyclic heterocyclic group which may be substituted with one or more groups selected from substituent group A1, further preferable.

$R^2$ represents a substituted $C_{3-8}$ cycloalkyl group which may be substituted, an aryl group which may be substituted, or a heterocyclic group which may be substituted.

The $C_{3-8}$ cycloalkyl group, the aryl group, and the heterocyclic group of $R^2$ may be substituted with one or more groups selected from substituent group A.

A compound in which $R^2$ represents an aryl group which may be substituted is preferable; a compound in which $R^2$ represents a phenyl group which may be substituted, more preferable; and a compound in which $R^2$ represents a phenyl group which may be substituted with one or more groups selected from substituent group A2, further preferable.

In another aspect, a compound in which $R^2$ represents a heterocyclic group which may be substituted is preferable; a compound in which $R^2$ represents a monocyclic heterocyclic group which may be substituted, more preferable; and a compound in which $R^2$ represents a monocyclic heterocyclic group which may be substituted with one or more groups selected from substituent group A2, further preferable.

$R^3$ represents a hydrogen atom or a carboxyl protecting group.

A compound in which $R^3$ represents a hydrogen atom is preferable.

An example of a salt of the compound represented by general formula [1] includes a generally known salt of a basic group, such as an amino group; or of an acidic group, such as a hydroxyl group or a carboxyl group.

Examples of a salt of the basic group include a salt with a mineral acid, such as hydrochloric acid, hydrobromic acid, nitric acid, and sulfuric acid; a salt with an organic carboxylic acid, such as formic acid, acetic acid, citric acid, oxalic acid, fumaric acid, maleic acid, succinic acid, malic acid, tartaric acid, aspartic acid, trichloroacetic acid, and trifluoroacetic acid; and a salt with a sulfonic acid, such as methanesulfonic acid, benzenesulfonic acid, p-toluenesulfonic acid, mesitylenesulfonic acid, and naphthalenesulfonic acid.

Examples of a salt of the acidic group include a salt with an alkali metal, such as sodium and potassium; a salt with an alkali earth metal, such as calcium and magnesium; an ammonium salt; and a salt with a nitrogen-containing organic base, such as trimethylamine, triethylamine, tributylamine, pyridine, N,N-dimethylaniline, N-methylpiperidine, 4-methylmorpholine, diethylamine, dicyclohexylamine, procaine, dibenzylamine, N-benzyl-6-phenethylamine, 1-ephenamine and N,N'-dibenzylethylenediamine.

Among the salts described above, a pharmacologically acceptable salt is preferable.

If the compound represented by general formula 1 has an isomer (such as an optical isomer, a geometric isomer, and a tautomer), the present invention embraces the isomer and also a solvate, a hydrate, and crystals in various shapes.

In addition, the present invention embraces a prodrug of the compound represented by general formula 1.

If the compound represented by general formula 1, or a salt thereof, is used as a pharmaceutical, a formulation adjuvant usually used in formulation, such as an excipient, a carrier, and a diluent, may be appropriately admixed.

The compound or salt thereof may be administered orally or parenterally in the form of a tablet, a capsule, a powder, a syrup, a granule, a pill, a suspension, an emulsion, a liquid, a powder formulation, a suppository, an eye drop, a nasal drop, an ear drop, a patch, an ointment, a lotion, a cream, or an injection. In addition, the method of administration, dosage, and number of doses may be appropriately selected in accordance with the age, weight, and symptoms of the patient. Usually, an adult may be administered a dose of 0.01 to 1000 mg/kg at a time or in several portions a day orally or parenterally (for example, administration by injection, by drip, and to a rectal region).

Next, a method for producing the compound represented by general formula 1 will be described.

The compound represented by general formula [1] is produced by a combination of known methods, and can be produced by, for example, the following production method:

Production Method 1

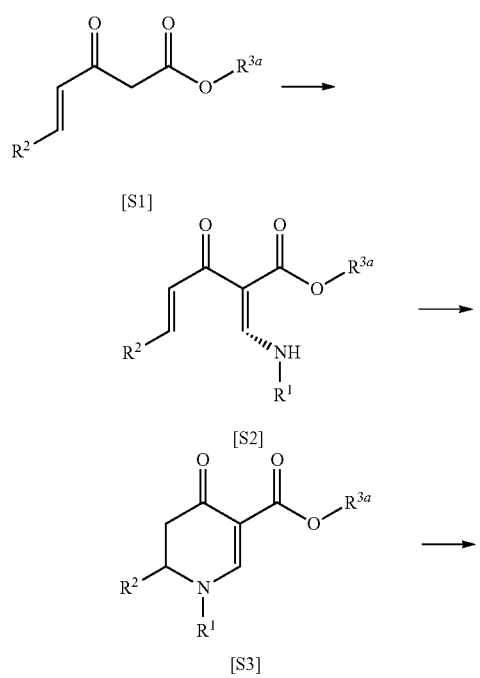

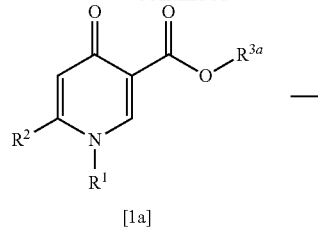

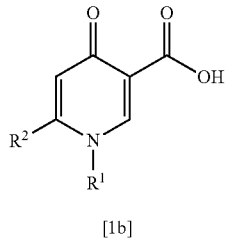

wherein $R^{3a}$ represents a carboxyl protecting group, and $R^1$ and $R^2$ have the same meanings defined above.

A compound represented by general formula [S2] can be produced by reacting a compound represented by general formula [S1] with an acetal, such as N,N-dimethylformamide dimethyl acetal, and then reacting the resultant with a compound represented by the general formula, $R^1NH_2$.

This reaction may be performed in accordance with a method described in Patent Document 1.

A compound represented by general formula [S3] can be produced by subjecting the compound represented by general formula [S2] to a ring-closing reaction.

This reaction may be performed in accordance with the method described in Patent Document 1.

A compound represented by general formula [1a] can be produced by subjecting the compound represented by general formula [S3] to a dehydrogenation reaction.

This reaction may be performed in accordance with the method described in Patent Document 1.

A compound represented by general formula [1b] can be produced by subjecting the compound represented by general formula [1a] to a deprotection reaction.

This reaction may be performed in accordance with the method described in Patent Document 1.

Next, the present invention will be described with reference to test examples. It should be noted that the present invention is not limited to the examples given.

Compounds 1 to 16 were used as test compounds.

Test Example 1: Anti-HBV Assay

The anti-HBV activity of compounds 1 to 16 was evaluated as follows by using HepG2.2.15 cells (Proc. Natl. Acad. Sci. USA, 84, 1005-1009, 1987), which are obtained by introducing the HBV genome into hepatoblastoma cell line, HepG2, and persistently produce the virus.

The following was used as a medium:

DMEM/F-12,GlutaMAX(manufactured by Invitrogen)+5 µg/mL insulin (manufactured by Wako)+1% penicillin/streptomycin(manufactured by Sigma)+10 mmol/L HEPES(manufactured by Sigma)+50 µmol/L hydrocortisone(manufactured by Sigma)+10% FBS A mixture of each test compound with dimethyl sulfoxide (DMSO) was added to the medium to obtain a final concentration of DMSO of 1% (v/v), and thus, test solutions containing the test compound in various concentrations were prepared. In addition, a test solution obtained by adding DMSO alone to the medium to obtain a final concentration of 1% (v/v) was prepared as a control without drug.

(1) The HepG2.2.15 cells were suspended in the medium and prepared a cell suspension at $1.5 \times 10^5$ cells/mL. The suspension was seeded in a 96-well microtiter plate (100 µL/well) and the plate was incubated in a 5% $CO_2$ incubator at 37° C. for 1 day.

(2) After removing the culture supernatant, the cells were washed twice with PBS(−) (100 µL/well) and then once with the medium (100 µL/well).

(3) Each test solution was added to the plate (100 µL/well), and the plate was incubated in a 5% $CO_2$ incubator at 37° C. for 3 days.

(4) After removing the culture supernatant, the test solution was added to the plate again (100 µL/well) and the plate was incubated in a 5% $CO_2$ incubator at 37° C. for 3 days.

(5) The culture supernatant was collected and treated with a mixture of Buffer AL (manufactured by QIAGEN) and Proteinase K (manufactured by Invitrogen). The amount of HBV DNA in the solution was quantified by real-time PCR. In addition, the amount of HBsAg (hepatitis B surface antigen) in the culture supernatant was quantified by chemiluminescent enzyme immunoassay using a Lumipulse HBsAg-HQ (manufactured by Fujirebio Inc.). The relative viral load (%) of a well with the compound to a well without the compound was calculated. An $IC_{50}$ of each compound was calculated using the FORECAST function (linear regression method) of Microsoft Excel 2007 by plotting the logarithm of the concentration against the relative viral load as a real number.

The results are shown in Table 1.

TABLE 1

| Compound No. | Structural formula | IC50 (µM) HBV-DNA | HBsAg |
|---|---|---|---|
| 1 | | 0.051 | 1.1 |
| 2 | | 0.16 | 0.79 |
| 3 | | 0.86 | 5.7 |
| 4 | | 0.088 | 2.1 |
| 5 | | 0.33 | 4.6 |
| 6 | | 1.1 | 5.8 |
| 7 | | 1.1 | 4.6 |
| 8 | | 0.25 | 1.2 |

TABLE 1-continued

| Compound No. | Structural formula | IC50 (μM) HBV-DNA | HBsAg |
|---|---|---|---|
| 9 | | 0.23 | 3.6 |
| 10 | | 2.1 | 6.9 |
| 11 | | 0.80 | 3.7 |
| 12 | | 1.4 | 4.9 |
| 13 | | 0.49 | 1.8 |
| 14 | | 0.91 | 4.2 |
| 15 | | 4.5 | 11 |
| 16 | | 7.9 | 35 |

Compounds 1 to 16 exhibited an excellent anti-HBV activity

Test Example 2: Anti-HBV Assay in PXB-Cells

The anti-HBV activity of compound 8 was evaluated as follows by using fresh human hepatocyte (The PXB-cells were produced by PhenixBio Co., Ltd.) derived from a PXB mouse (a chimeric mouse with human hepatocyte).

The following was used as a medium:

500 mL DMEM (manufactured by Sigma)+0.25 μg/mL insulin (manufactured by Wako)+1% penicillin/streptomycin. (manufactured by Sigma)+20 mmol/L HEPES (manufactured by Sigma)+15 μg/mL L-proline (manufactured by Sigma)+50 nmol/L dexamethasone (manufactured by Sigma)+5 ng/mL EGF (manufactured by Peprotech)+0.1 mmol/L ascorbic acid 2-phosphate (manufactured by Wako)+10% FBS+2% DMSO Compound 8 was further added to the medium to prepare a 10 μmol/L test solution.

(1) The PXB-cells seeded at a $2.1 \times 10^5$ cells/cm$^2$ in a 48-well microliter plate were incubated in a 5% CO$_2$ incubator at 37° C. for 5 days.

(2) HBV derived from PXB mouse serum (genotype AeUS) was added to the medium supplemented with 4% PEG-8000. The PXB cells were infected with this solution at about 10 copies/cell (250 μL/well) and the plate was incubated in a 5% CO$_2$ incubator at 37° C. for 1 day.

(3) After the culture supernatant had been removed, the cells were washed three times with DMEM supplemented with 10% FBS and 1% penicillin/streptomycin. The medium was added to the plate (250 μL/well) and the plate was incubated in a 5% $CO_2$ incubator at 37° C. for 1 day.

(4) After removing the culture supernatant, the cells were washed three times with DMEM supplemented with 10% FBS and 1% penicillin/streptomycin. The medium was added to the plate (250 μL/well) and the plate was incubated in a 5% $CO_2$ incubator at 37° C. for 5 days.

(5) After the culture supernatant had been removed, the medium was added to the plate (250 μL/well) and the plate was incubated in a 5% $CO_2$ incubator at 37° C. for 5 days.

(6) After the culture supernatant on day 12 post infection was removed, the medium was added to the plate (250 μL/well), and the plate was incubated in a 5% $CO_2$ incubator at 37° C. for 5 days.

(7) After the culture supernatant on day 17 post infection was removed, the test solution was added to the plate (250 μL/well) and as a control without drug, the medium was added to the plate (250 μL/well). The plate was incubated in a 5% $CO_2$ incubator at 37° C. for 5 days.

(8) After the culture supernatant on day 22 post infection was removed, the test solution added to the plate (250 μL/well) and as a control without drug, the medium was added to the plate (250 μL/well). The plate was incubated in a 5% $CO_2$ incubator at 37° C. for 5 days.

(9) After the culture supernatant on day 27 post infection was removed, the test solution added to the plate (250 μL/well) and as a control without drug, the medium was added to the plate (250 μL/well). The plate was incubated in a 5% $CO_2$ incubator at 37° C. for 5 days.

(10) The culture supernatant on day 32 post infection was collected.

(11) The collected culture supernatant on day 32 post infection was purified using a QIAamp DNA Blood Mini Kit (manufactured by QIAGEN) and the amount of HVB DNA was quantified by real-time PCR. In addition, the amount of HBsAg (hepatitis B surface antigen) in the culture supernatant was quantified by chemiluminescent enzyme immunoassay using a Lumipulse HBsAg-HQ (manufactured by Fujirebio Inc.). The relative viral load (%) of a well with the compound to a well without the compound was calculated.

The relative viral load was 16% with respect to the amount of HBV DNA, and 29% with respect to the amount of HBsAg. Thus, compound 8 exhibited excellent anti-HBV activity.

INDUSTRIAL APPLICABILITY

A compound represented by general formula [1] or a salt thereof shows excellent anti-HBV activity and is useful as an anti-hepatitis B virus agent.

The invention claimed is:

1. A method of treating hepatitis B virus, the method comprising administering an anti-hepatitis B virus agent to a patient in need thereof, the anti-hepatitis B virus agent comprising a compound represented by general formula [1]:

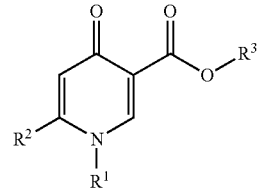

[1]

wherein $R^1$ represents an aryl group which may be substituted or a heterocyclic group which may be substituted;

$R^2$ represents a $C_{3-8}$ cycloalkyl group which may be substituted, an aryl group which may be substituted, or a heterocyclic group which may be substituted; and $R^3$ represents a hydrogen atom or a carboxyl protecting group, or a salt thereof.

2. The method according to claim 1, wherein $R^1$ represents an aryl group which may be substituted.

3. The method according to claim 1, wherein $R^1$ represents a phenyl group which may be substituted.

4. The method according to claim 1, wherein $R^1$ represents a heterocyclic group which may be substituted.

5. The method according to claim 1, wherein $R^1$ represents a bicyclic heterocyclic group which may be substituted.

6. The method according to claim 1, wherein $R^2$ represents an aryl group which may be substituted.

7. The method according to claim 1, wherein $R^2$ represents a phenyl group which may be substituted.

8. The method according to claim 1, wherein $R^2$ represents a heterocyclic group which may be substituted.

9. The method according to claim 1, wherein $R^2$ represents a monocyclic heterocyclic group which may be substituted.

* * * * *